United States Patent [19]

Katz

[11] 4,287,175

[45] Sep. 1, 1981

[54] CONTACT LENS WETTING AGENTS

[75] Inventor: Irving M. Katz, Lansdale, Pa.

[73] Assignee: Merck & Co., Inc., Rahway, N.J.

[21] Appl. No.: 44,620

[22] Filed: Jun. 1, 1979

Related U.S. Application Data

[63] Continuation of Ser. No. 918,121, Jun. 22, 1978, abandoned, which is a continuation of Ser. No. 600,167, Jul. 29, 1975, abandoned.

[51] Int. Cl.³ .............. A61K 31/70; A61K 31/74; A61K 31/78; A61K 47/00
[52] U.S. Cl. ............................. 424/78; 424/80; 424/81; 424/180; 424/362
[58] Field of Search .................. 424/78, 80, 81, 362, 424/180

[56] References Cited

U.S. PATENT DOCUMENTS

| | | | |
|---|---|---|---|
| 2,703,777 | 3/1955 | Feinstein et al. | 424/145 |
| 3,767,788 | 10/1973 | Rankin | 424/78 |
| 3,845,201 | 10/1974 | Haddad | 424/22 |
| 3,856,919 | 12/1974 | Rankin | 424/78 |
| 3,863,633 | 2/1975 | Ryde et al. | 424/78 |
| 3,868,445 | 2/1975 | Ryde et al. | 424/78 |
| 3,875,300 | 4/1975 | Homm et al. | 424/28 |
| 3,911,098 | 10/1975 | Capozza | 424/22 |
| 3,920,810 | 11/1975 | Rankin | 424/80 |
| 3,935,303 | 1/1976 | Khromov et al. | 424/78 |
| 3,947,573 | 3/1976 | Rankin | 424/80 |
| 3,978,201 | 8/1976 | Khromov et al. | 424/78 |
| 3,987,163 | 10/1976 | Rankin | 424/78 |
| 3,991,759 | 11/1976 | Urguhart | 128/260 |
| 4,003,991 | 1/1977 | Kromov et al. | 424/81 |
| 4,039,662 | 8/1977 | Hecht et al. | 424/180 |

OTHER PUBLICATIONS

Maichak; Invest. Ophthal. 14(2) (1975). Ophthalmic Drug Inserts.
Lemp et al. Chem. Abst. 76 90019(j) (1972).
Lofholm, "Ophthalmic Products"-Handbook of Non--Prescription Drugs (1973) Pub. Am. Pharm. Assoc. pp. 99–107.
Chem. Abst. 83 136920(w) (1975)–Cohen et al.
Int. Ophthal. Clin. 13 145–153 (1973)–Lemp, Tear Substitutes . . .
Int. Ophthal. Clin. 13 221–229 (1973)–Lemp, Artificial Tear Solutions.
Int. Ophthal. Clin. 13 231–237 (1973)–Pavan–Langston.

*Primary Examiner*—Douglas W. Robinson
*Attorney, Agent, or Firm*—Edmunde D. Riedl; Mario A. Monaco

[57] ABSTRACT

A method of wetting a contact lens present in the human eye which comprises inserting a water soluble solid polymer into the cul-de-sac of the eye.

5 Claims, No Drawings

CONTACT LENS WETTING AGENTS

This is a continuation of application Ser. No. 918,121, filed June 22, 1978, now abandoned which is a continuation of U.S. Ser. No. 600,167, filed July 29, 1975, now abandoned.

BACKGROUND OF THE INVENTION

Many advances have been made in recent years in the fitting of contact lenses. Nonetheless most contact lens wearers begin to feel some discomfort when wearing these contact lenses after a short period of time. In addition because of the hydrophobic nature of the lens the natural tear film of the eye is not able to properly coat the lenses leading to reduced visual accuity, irritation and with the prolonged use of contact lenses edema of the corneal epithelium.

In order to reduce irritation, insure comfort and increase visual accuity when wearing contact lenses, various wetting solutions have been suggested. These solutions have been applied to the contact lens before insertion into the eye and have also been applied to the eye. These wetting solutions have primarily involved the use of polyvinylalcohol as wetting agents and various cellulose derivatives as viscosity building agents. A recent U.S. Pat. No. 3,549,747 describes an aqueous wetting solution containing polymeric viscosity building agents. Although these solutions tend to eliminate the conditions described hereinabove, like all previous wetting solutions the effect of these solutions is short lived.

Solid polymeric water soluble inserts placed in the eye of a patient wearing contact lenses acts as a wetting agent and is effective in improving clarity of vision, improve lens wearing comfort and wearing time over a much longer period of time than heretofore possible with wetting solutions.

This polymer insert, therefore when inserted in the cul-de-sac of the eye present concurrently while wearing the contact lens slowly dissolves, affording a continuous long term release of artificial tears and thereby maintaining the wetness of the lens while in the eye, providing better tear circulation and resulting in improved and more efficient metabolic exchange.

It has been surprisingly found that a non-toxic water soluble solid polymer inserted into the cul-de-sac of the eye is effective in relieving the symptoms mentioned herein. It was not expected that such a polymer, which in the past had been used merely as a viscosity agent, could in a solid form act by itself to relieve such symptoms. It has also been surprising to find that such a water soluble polymer in solid form while uniformly dissolving in the eye would provide the necessary wettability of the contact lens for a period of at least several hours.

DETAILS OF THE INVENTION

This invention relates to a method of improving clarity of vision of contact lens wearers, for improving the lens wearing comfort and wearing time by applying a non-toxic solid water soluble polymer ophthalmic insert into the cul-de-sac of the eye to obtain long term release of a wetting agent. The polymer used to form the inserts of this invention may be any water soluble non-toxic polymer. For example, one may employ water soluble polymers of cellulose derivatives such as methylcellulose, sodium carboxymethyl cellulose, hydroxyloweralkyl cellulose, hydroxyethyl cellulose, hydroxypropyl cellulose, hydroxypropylmethyl cellulose; arcrylates such as polyacrylic acid salts, ethylacrylates, polyacrylamides; natural products such as gelatin, alginates, pectins, tragacanth, karaya, chrondrus, agar, acacia; the starch derivatives such as starch acetate, hydroxyethyl starch ethers, hydroxypropyl starch, as well as other synthetic derivatives such as poly vinyl alcohol, poly vinyl pyrrolidone, poly vinyl methyl ether, poly ethylene oxide, neutralized carbopol and xanthan gum, mixtures of said polymer.

Preferably the solid insert is prepared from cellulose derivatives such as methylcellulose, hydroxyethyl cellulose, hydroxypropyl cellulose or hydroxypropylmethyl cellulose or from other synthetic materials such as poly vinyl alcohol, poly vinyl pyrrollidone, polyethylene oxide or poly vinyl methylether. Hydroxypropyl cellulose, one of the preferred polymers for the preparation of the insert of the invention is available in several polymeric forms, all of which are suitable in the preparation of these inserts. Thus the product sold by Hercules, Inc. of Wilmington, Delaware under the name KLUCEL such as KLUCEL HF, HWF, MF, GF, JF, LF and EF which are intended for food or pharmaceutical use are particularly useful in preparing the inserts of this invention. The molecular weight of these polymers useful for the purposes described herein may be at least 30,000 to about 1,000,000 or more. Similarly, an ethylene oxide polymer having a molecular weight of up to 5,000,000 or greater, and preferably 100,000 to 5,000,000 can be employed. Further, for example, POLYOX a polymer supplied by Union Carbide Co. may be used having a molecular weight of about 50,000 to 5,000,000 or more and preferably 3,000,000 to 4,000,000. Other specific polymers which are useful in this invention are polyvinylpyrrolidine having a molecular weight of from about 10,000 to about 1,000,000 or more, preferably up to about 350,000 and especially about 20,000 to 60,000; polyvinyl alcohol having a molecular weight of from about 30,000 to 1,000,000 or more, particularly about 400,000 and especially from about 100,000 to about 200,000; hydroxypropylmethyl cellulose having a molecular weight of from about 10,000 to 1,000,000 or more, particularly up to about 200,000 and especially about 80,00 to about 125,000; methyl cellulose having a molecular weight of from about 10,000 to about 1,000,000 or more, preferably up to about 200,000 and especially about 50 to 100,000; and CARBOPOL (carboxyvinyl polymer) of B. F. Goodrich and Co. designated as grades 934, 940 and 941. It is clear that for the purpose of this invention the molecular weight of the polymer is not critical. Water soluble polymers can be used having an average molecular weight which will afford dissolution of the polymer in any desired length of time. The inserts, therefore, can be prepared to allow for retention and accordingly effectiveness in the eye for any desired period.

The insert can be of any desired shape and size which can readily fit into the eye and particularly the conjunctival sac while not blocking the contact lens. Accordingly, the insert can be in the form of a square, rod, rectangle, oval, circle, doughnut, semicircle, ¼ moon shape, and the like. Preferably, the insert is in the form of a rod, doughnut, oval or ¼ moon. The insert can be readily prepared, for example, by dissolving the polymer in a suitable solvent and the solution evaporated to afford a thin film of the polymer which can then be subdivided to prepare inserts of appropriate size. Alternatively, the insert can be prepared by warming the polymer and then molded to form a thin film. Preferably, the inserts are prepared by molding or extrusion procedures well known in the art. The molded or extruded product can then be subdivided to afford inserts of suitable size for administration in the eye. In order to properly fit into the cul-de-sac of the eye without excessive irritation, and yet to be effective for its intended use, the insert should have a surface area of from about 5 to about 400 sq. mm. preferably 10-200 and especially 10-100 sq./mm., a length of from about 1-30 mm. and preferably about 5-20 mm., and a width and height of from about 0.25 mm. to about 30 mm., preferably from about 1-10 mm. and especially 1-5 mm. The inserts may contain from 1-1000 mg. of water soluble polymer, preferably 5-300 mg. and especially 5-100 mg. The time of dissolution of the insert is dependent upon each patients natural supply of tears as well as the size and the particular polymer employed. Usually the time of dissolution is between about 4 hours and 7 days, and preferably 6 to 24 hours. For example, castings or compression molded films having a thickness of about 0.25 mm. to 15.0 mm. can be subdivided to obtain suitable inserts. Rectangular segments of the cast or compressed film having a thickness between about 0.5 and 1.5 mm. can be cut to afford shapes such as rectangular plates of 4×5-20 mm. or ovals of comparable size. Similarly, extruded rods having a diameter between about 0.5 and 1.5 mm. can be cut into suitable sections to provide the desired amount of polymer. For example, rods of 1.0 to 1.5 mm. in diameter and about 20 mm. long are found to be satisfactory. The inserts may also be directly formed by injection molding. It is preferred that the ophthalmic inserts of the present invention be formed so that they are smooth and do not have any sharp edges or corners which could cause damage to the eye. Since the term smooth and sharp edges or corners are subjective terms, in this application these terms are used to indicate that excessive irritation of the eye will not result from the use of the insert.

The ocular inserts of this invention can also contain plasticizers, buffering agents and preservatives. Plasticizers suitable for this purpose must, of course, also be completely soluble in the lacrimal fluids of the eye. Examples of suitable plasticizers that might be mentioned are water, polyethylene glycol, propylene glycol, glycerine, trimethylol propane, di and tripropylene glycol, hydroxypropyl sucrose and the like. Typically, such plasticizers can be present in the ophthalmic insert in an amount ranging from up to 1 about 30% by weight. A particularly preferred plasticizer is water which is present in amounts of at least about 5% up to about 40%. In actual practice, a water content of from about 10% to about 20% is preferred since it may be easily accomplished and adds the desired softness and pliability to the insert.

When plasticizing the solid product with water, the product is contacted with air having a relative humidity of at least 40% until said product picks up at least about 5% water and becomes softer and more pliable. In a preferred embodiment, the relative humidity of the air is from about 60% to about 99% and the contacting is continued until the water is present in the product in amounts of from about 10% to about 20%.

Suitable water soluble preservatives which may be employed in the insert are sodium bisulfate, sodium thiosulfate, ascorbate, benzalkonium chloride, chlorobutanol, thimerosal, phenylmercuric acetate, phenylmercuric borate, parabens, benzyl alcohol and phenylethanol. These agents may be present in amounts of from 0.001 to 5% by weight of solid insert, and preferably 0.1 to 2%.

Suitable water soluble buffering agents are alkali, alkali earth carbonates, phosphates, bicarbonates, citrates, borates, and the like, such as sodium phosphate, citrate, borate, acetate, bicarbonate and carbonate. These agents may be present in amounts sufficient to obtain a pH of the system of between 5.5 to 8.0 and especially 7-8; usually up to about 2% by weight of polymer.

The following examples are given by way of illustration.

EXAMPLE 1

Hydroxypropyl Cellulose Inserts

Cylindrical rod-shaped ophthalmic inserts are prepared by an injection molding procedure as described below:

The powdered hydroxypropyl cellulose (KLUCEL GF) is heated in a cup to 200° C. When the powder is melted and begins to flow, the valve at the outlet of the cup is opened and the molten mass is forced into a mold under the action of both pressure and the elastic melt extruder effect. The mold is then removed from the machine and opened. The specimen is removed from the mold and has a diameter of 1.25 mm. The specimen is cut into lengths of 10 mm. having a weight of about 12 mg. The ophthalmic inserts are plasticized by placing them into an 88% relative humidity cabinet for two days where they pick up 10-16% moisture.

Similar inserts are prepared having a diameter of 1.0 to 1.5 mm. and a length of 15, 20 and 23 mm.

EXAMPLE 2

Hydroxypropyl Cellulose Inserts

Ophthalmic inserts are prepared by the compression molding procedure as described below:

Compression molded films are prepared on a Hydraulic Press by subjecting hydroxypropyl cellulose (KLUCEL HF) to a compressional force of 12,000 lbs. (gauge) at 300° F. for one to two minutes. The film is cooled under pressure by having cold water circulate in the platen. Film thickness is controlled by placing shims between the upper and lower compression plates holding the hydroxypropyl cellulose. Ophthalmic inserts are then individually cut from the film with a rectangular shaped punch, to afford individual inserts having a thickness of 0.55 mm., width of 2 mm., length of 12.5 mm. and a weight of about 12.5 mg.

EXAMPLE 3

Hydroxypropyl Cellulose Inserts

Ophthalmic inserts are prepared by a film casting procedure as described below:

A 1% (w/v) aqueous solution of hydroxypropyl cellulose (KLUCEL JF) is prepared and then poured onto a glass plate. The glass plate is then placed into a 50° C. hot air cabinet for 16 hours and the water is allowed to evaporate.

The resulting film is removed from the glass plate and ophthalmic inserts are then individually cut from the film with an oval shaped punch. The final insert has a diameter of 1.0 mm., length of 10 mm. and a weight of 7.0 mg.

EXAMPLE 4

Hydroxypropyl Cellulose Inserts

Cylindrical rod-shaped ophthalmic inserts are prepared by the extrusion procedure as described below:

The hydroxypropyl cellulose (KLUCEL HF) is fed into a screw extruder whose barrel is heated at 400°–450° F. The hydroxypropyl cellulose is melted and then extruded through an orifice (0.04 inch to 0.65 inch). The extrudate while hot is then sized to form a monodiameter filament, which is then cut into 12 mm. lengths having a diameter of 1.0 mm. and a weight of 12.0 mg. The ophthalmic inserts are plasticized by placing them into an 88% relative humidity cabinet for two days where they pick up 10–15% moisture.

In a similar fashion, rod-shaped inserts are prepared having the following dimensions: length 12.0 mm., diameter 1.25 and 1.50 mm. and weight of about 15 and 21 mg., respectively.

EXAMPLE 5

Poly Vinyl Alcohol Inserts

Cylindrical rod-shaped ophthalmic inserts are prepared by the injection molding procedure as described below:

The powdered poly vinyl alcohol average molecular weight of 125,000 is heated in a cup 190°–200° C. When the powder is melted and begins to flow, the valve at the outlet of the cup is opened and the molten mass is forced into a mold under the action of both pressure and the elastic melt extruder effect. The mold is then removed from the machine and opened. The specimen that is removed from the mold is cut into lengths of 10 mm. having a diameter of 1.25 mm. and weight of 12 mg. The ophthalmic inserts are plasticized by placing them into an 88% relative humidity cabinet for two days where they pick up 10–15% moisture.

In a similar fashion, rod-shaped inserts are prepared having a length of 10 mm., a diameter of 1.0 and 1.5 mm. and a weight of 8 and 18 mg., respectively.

EXAMPLE 6

Hydroxypropylmethyl Cellulose Inserts

Ophthalmic inserts are prepared by a film casting procedure as described below:

A 1% (w/v) aqueous solution of hydroxypropyl cellulose (Methocel HG 60) is prepared and then poured onto a glass plate. The glass plate is then placed into a 50° C. hot air cabinet for 16 hours and the water is allowed to evaporate.

The resulting film is removed from the glass plate and ophthalmic inserts are then individually cut from the film with a rectangular shaped punch to afford rectangular inserts having a length of 12.5 mm., height of 0.55 mm., width of 2 mm. and weight of 14 mg.

Methocel HG 60 is a commercial methyl cellulose product manufactured by the Dow Chemical Company and has a methoxyl percentage of 28–30%, a hydroxypropyl percentage of 7–12% is soluble in $H_2O$ and organic solvents, has a normal gel temperature of 60° F. and demonstrates an average viscosity of 50 centipoises (range 40–60, 2% aqueous solution).

EXAMPLE 7

Methyl Cellulose Inserts

Ophthalmic inserts are prepared by a film casting procedure as described below:

A 1% (w/v) aqueous solution of methyl cellulose (average molecular weight 75,000) is prepared and then poured onto a glass plate. The glass plate is then placed into a 50° C. hot air cabinet for 16 hours and the water is allowed to evaporate.

The resulting film is removed from the glass plate and ophthalmic inserts are then individually cut from the film with a rod-shaped punch. The insert has a diameter of 1 mm., a length of 8 mm. and weight of 6 mg.

EXAMPLE 8

Hydroxypropyl Cellulose 90% Propylene Glycol 10%

Ophthalmic inserts are prepared by a film casting procedure as described below:

A 0.1% (w/v) aqueous solution of hydroxypropyl cellulose (KLUCEL HF) is prepared to contain 0.1% by weight propylene glycol and then poured onto a glass plate. The glass plate is then placed into a 50° C. hot air cabinet for 16 hours and the water is allowed to evaporate.

The resulting film is removed from the glass and ophthalmic inserts are then individually cut from the film with a round-shaped punch. The inserts have a diameter of 0.9 mm. and weight of 22 mg.

EXAMPLE 9

Hydroxypropyl Cellulose (HF) 90% Glycerine 10%

Cylindrical rod-shaped ophthalmic inserts are prepared by an extrusion procedure as described below:

The hydroxypropyl cellulose/glycerine mixture is fed into a $\frac{3}{4}''$ single screw extruder whose barrel is heated to 300°–350° F. The mixture is melted and then extruded through an orifice (0.04 inch to 0.065 inch). The extrudate while hot is then sized to form a monodiameter filament, which is then cut into lengths of 6 mm. having a diameter of 1.5 mm. and a weight of 11 mg.

EXAMPLE 10

Poly Ethylene Oxide Inserts

Ophthalmic inserts can be prepared by a film casting procedure as described below:

A 1% (w/v) aqueous solution of poly ethylene oxide having an average molecular weight of 1,000,000 is prepared and then poured onto a glass plate. The glass plate is then placed into a 50° C. hot air cabinet for 16 hours and the water is allowed to evaporate.

The resulting film is removed from the glass plate and ophthalmic inserts are then individually cut from the film with a rod-shaped punch. The insert has a diameter of 1 mm., a length of 6 mm. and a weight of 9 mg.

EXAMPLE 11

Benzalkonium Chloride 0.02% Hydroxypropyl Cellulose 9.98

Ophthalmic inserts are prepared by a film casting procedure as described below:

A 1% (w/v) aqueous solution of hydroxypropyl cellulose (KLUCEL GF) is prepared to contain 0.02% by weight benzalkonium chloride and then poured onto a glass plate. The glass plate is then placed into a 50° C.

hot air cabinet for 16 hours and the water is allowed to evaporate.

The resulting film is removed from the glass plate and ophthalmic inserts are then individually cut from the film with a rod-shaped punch. The diameter of the insert is 1.25 mm., length of 6 mm. and weight 7 mg. The ophthalmic inserts are plasticized by placing them into an 88% relative humidity cabinet for two days where they pick up 10–15% moisture.

EXAMPLE 12

Carboxypolymethylene Inserts

Ophthalmic inserts are prepared by a film casting procedure as described below:

A 1% (w/v) aqueous solution of carboxypolymethylene (average molecular weight 3 million) is prepared and then poured onto a glass plate. The glass plate is then placed into a 50° C. hot air cabinet for 16 hours and the water is allowed to evaporate.

The resulting film is removed from the glass plate and ophthalmic inserts are then individually cut from the film with a rectangular shaped punch. The insert has a length of 12.5 mm., a height of 0.7 mm., width of 2 mm. and weight of 18 mg. The ophthalmic inserts are plasticized by placing them into an 88% relative humidity cabinet for two days where they pick up 10–15% moisture.

EXAMPLE 13

Sodium Carbonate (anhydrous) 0.25% Hydroxypropyl Cellulose (KLUCEL GF) 9.75

Ophthalmic inserts can be prepared by a compression molding procedure as described below:

Compression molded films are prepared on a Carver Press by subjecting the hydroxypropyl cellulose/sodium carbonate (anhydrous) mixture to a compressional force of 12,000 lbs. (gauge) at 300° F. for one to two minutes. The film is cooled under pressure by having cold water circulate in the platen. Film thickness is controlled by placing shims between the upper and lower compression plates holding the hydroxypropyl cellulose. Ophthalmic inserts are then individually cut from the film with a rod-shaped punch. The insert has a diameter of 1.25 mm., a length of 10 mm. and weight of 12 mg. The ophthalmic inserts are plasticized by placing them into an 88% relative humidity cabinet for two days where they pick up 10–15% moisture.

What is claimed is:

1. A method for improving the comfort and wearing time of contact lenses comprising inserting into the eye of a contact lens wearer an insert consisting essentially of a solid polymer which is soluble in lacrimal fluids having a surface area of from about 5 to about 800 sq. mm., a length of from about 1–30 mm. and a width of height of from about 0.25 mm. to about 30 mm., said polymer being selected from the group consisting of cellulose derivatives, natural gums, starch derivatives, dextrose, polyalkylene glycols, polyvinylmethyl ethers, polyethylene oxide, acrylates, xanthan gums and mixtures thereof.

2. The method of claim 1 wherein the polymer is hydroxypropyl cellulose.

3. The method of claim 1 having between 1–40% by weight of water.

4. The method of claim 1 wherein the water content is between 5–20%.

5. The method according to claim 2 where the hydroxypropyl cellulose has a molecular weight of from 10,000 to 1,000,000.

* * * * *